United States Patent

Blanchard et al.

Patent Number: 5,151,164
Date of Patent: Sep. 29, 1992

[54] ENHANCED CAPILLARY ZONE ELECTROPHORESIS AND APPARATUS FOR PERFORMANCE THEREOF

[75] Inventors: William C. Blanchard, Phoenix; Cheng S. Lee, Columbia, both of Md.

[73] Assignees: The University of Maryland, College Park; Blanchard and Co., Phoenix, both of Md.

[21] Appl. No.: 477,755

[22] Filed: Feb. 9, 1990

[51] Int. Cl.$^5$ ............................................. G01N 27/26
[52] U.S. Cl. .............................. 204/182.1; 204/180.1; 204/182.2; 204/299 R
[58] Field of Search ............. 204/299 R, 180.1, 182.2, 204/182.1

[56] References Cited

U.S. PATENT DOCUMENTS

| | | | |
|---|---|---|---|
| 4,859,301 | 8/1989 | Brenner et al. | 204/180.1 |
| 4,898,658 | 2/1990 | Karger et al. | 204/299 R |
| 4,931,328 | 6/1990 | Swedberg | 204/180.1 |

FOREIGN PATENT DOCUMENTS

0137143  10/1981  Japan ............................. 204/299 R

OTHER PUBLICATIONS

Terabe et al., Electrokinetic Separations with Micellar Solutions and Open-Tubular Capillaries, Jan., 1984 111-113.

Terabe et al., Electrokinetic Chromatography with Micellar Solution and Open-Tubular Capillaries, Apr. 1985, 834-841.

Primary Examiner—John Niebling
Assistant Examiner—Arun S. Phasge
Attorney, Agent, or Firm—Oblon, Spivak, McClelland, Maier & Neustadt

[57] ABSTRACT

Capillary zone electrophoresis is enhanced by the application of an electric field across the interior of the capillary tube. This external electric field is applied through a conductive member at the exterior of the capillary tube. The external field vectorially couples with the internal field, controlling the polarity and the magnitude of the surface (zeta) potential on the interior surface of the capillary. The control of the surface (zeta) potential reduces adsorption of macromolecular onto the interior surface of the capillary tube, by inducing electrostatic repulsions between the macromolecules, and the capillary surface. Additionally, the control of the surface (zeta) potential can retard, and even reverse, electroosmotic flow, depending upon the magnitude of those fields.

13 Claims, 4 Drawing Sheets

ENHANCED CAPILLARY ZONE ELECTROPHORESIS AND APPARATUS FOR PERFORMANCE THEREOF

BACKGROUND OF THE INVENTION

1. Field of the Invention:

This invention pertains to capillary electrophoretic resolution processes. In particular, capillary zone electrophoresis, such as that employed to separate proteins and DNA fragments, micellar electrokinetic capillary chromatography and related resolution processes, are enhanced by the application of one or more electric fields across the capillary tube, in addition to the linear field applied along the tube, by means exterior to the interior surface of the tube. The application of these potentials across the tube substantially prevents adsorption of macromolecules, such as proteins, and allows control over the electroosmotic flow rate, enhancing separation resolutions and efficiencies.

2. Background of the Prior Art:

Capillary Zone Electrophoresis (CZE) performs such functions as quality control of recombinant proteins, evaluation of the purity of synthetic peptides, studying serum proteins, evaluating DNA fragments, checking biological degradation, analyzing drugs, monitoring antibodies, and studying bioactive peptides with the resolving power of electrophoresis and the ease and speed of High Performance Liquid Chromatography (HPLC). The low volume capability, high separation efficiency, and sensitive detection schemes make CZE a powerful method for analytical biotechnology, a critical need for today's bioindustry.

A fundamental problem in CZE is controlling electroosmosis, the flow of solvent in an applied potential field. Under normal aqueous conditions with small binary electrolytes, the silica surface has an excess of anionic charge resulting from ionization of surface functional groups. The cationic counter-ions to these anions are in the diffuse layer adjacent to the capillary walls. The potential across the diffuse layer is termed the zeta potential. These hydrated cations migrate towards the cathode and drag solvent with them. Thus, the direction and rate of electroosmotic flow are dependent on the polarity and magnitude of the zeta potential at the capillary walls.

Electroosmotic flow affects the amount of time a solute resides in the capillary and in this sense both the separation efficiency and resolution are related to the direction and flow rate of electroosmosis. If the rate of electroosmotic flow is greater in magnitude and opposite in direction to the electrophoretic mobilities of all anions in the buffer, then all ions will migrate in the same direction. Thus, electroosmosis results in better resolution of anions which migrate against the electroosmotic flow. Conversely, cations will be more poorly resolved under these conditions. In fact, good resolution of substances having very similar mobilities can be achieved by balancing electroosmotic flow against electrophoretic migration. The invention of this application provides this control.

In addition to controlling electroosmosis, application of CZE to the separation of proteins is complicated by adsorption of the minute quantities of the protein sample onto the walls of the capillary. Such interactions result in band broadening and tailing, with greatly reduced separation efficiency. Reported attempts to eliminate this sorption involve deactivation of the silica capillaries by physically coating the capillary wall with methylcellulose, as well as via silane derivation. Because of the inherent difficulty of reproducibly deactivating the capillary surface, alternative methods employing dynamic reduction of protein/capillary interactions have been developed. These include the addition of chemical reagents to the separation buffer, as well as manipulation of the charges on the proteins and the silica capillary wall to prevent adsorption by Coulombic repulsion.

Similarly, capillary electrokinetics have been used to resolve non-ionic mixtures, as well as ionic species, through partition phenomena with micelles. The process involving the use of micelles is called the micellar electrokinetic capillary chromatography (MECC). See, e.g., Wallingford et al, *Journal of Chromatoqraphy*, 441, p. 299 et. seg. (1988).

SUMMARY OF THE INVENTION

Capillary electrophoretic processes are improved by the application of an electric potential at the inside walls of the capillary. This is achieved by application of an electric field across a conductive element located on the exterior of the capillary tube in which electrophoresis is to be carried out. The coupling of this external electric field with the linear field, applied internally produces an electric field across the sidewalls of the capillary. This potential at the sidewalls along the tube controls the polarity and the magnitude of the surface (zeta) potential on the interior surface of the sidewall, and in fact, repels or attracts the ions of interest, and repels macromolecules, away from the surface, preventing adsorption onto the capillary wall.

Simultaneously, the direction and flow rate of electroosmotic flow can be controlled by using the external electric field applied from outside the capillary. This is because the direction and flow rate of electroosmotic flow is dependent upon the polarity and the magnitude of the surface (zeta) potential. This can greatly enhance the dwell time of the molecules to be separated in the electric field, resulting in increased resolution to the process. Thus, conventional apparatus is modified, by providing a means for applying an electric field from the exterior to the interior of the capillary tube, said means being located on the exterior of the capillary tube, and being in electrical connection with a means for a difference in potential to create said electric field.

DNA resolution is improved by retarding electroosmotic flow. Further, dynamic control over the speed of electroosmosis during the separation of DNA fragments, will increase resolving power. A slower electroosmosis from anode to cathode will be applied initially during the separation for enhancing the separation resolution of larger DNA fragments. This is to retain larger DNA fragments in the capillary, giving a longer time for zones to separate. When the larger DNA fragments migrate through the detector, a faster electroosmosis determined by the applied field will then be applied for decreasing the analysis time of smaller DNA fragments. This is because the smaller DNA fragments with larger electrophoretic mobility difference need less time for zones to separate. The ability to vary the speed (even the direction if it is necessary) of electroosmosis dynamically enhances separation resolution and efficiency and provides a tool to achieve innovative separation results for biomolecules.

In particular embodiments, the capillary tube is provided with a conductive coating, such as a metal coating, on the exterior, connected to a high voltage power source of electricity at one end of this coating. The coating at the other end of the capillary is connected through a suitable resistor to ground. Upon application of voltage from the power supply, current flows through the conductive coating. The resistance value of a suitable resistor is such that the potential at every point along the outside conductive coating differs from the potential at the electrolyte solution inside the capillary by a constant. This difference in potential between the inside and outside of the capillary provides an electric field across the capillary that is uniform and constant along the length of the capillary. This electric field across the sidewalls of the capillary controls the polarity and the magnitude of the surface (zeta) potential on the interior surface of the sidewall. This prevents adsorption, allowing the use of simple fused silica tubes, instead of the elaborate devices currently required. Because the direction and rate of electroosmotic flow is dependent upon the polarity and the magnitude of the surface (zeta) potential, application of these external electric fields enhances, retards and/or changes the direction of, electroosmotic flow through the capillary tube. The ability to manipulate the direction and flow rate of the electroosmosis enhances separation resolution.

DETAILED DESCRIPTION OF THE INVENTION:

This invention contemplates capillary electrophoresis apparatus which can be employed in the electrophoretic resolution of a wide variety of solutions and suspensions, including but not limited to the separation of DNA fragments, proteins and polypeptides, and generally both neutral and ionic molecules. The enhanced capillary zone electrophoretic apparatus and process of this invention can be used to perform such diverse functions as quality control of recombinant proteins, evaluation of the purity of synthetic peptides, studying serum proteins, evaluating DNA fragments, checking biological degradation, analyzing drugs, monitoring antibodies, and studying bioactive peptides with the resolving power of electrophoresis and the ease and speed of HPLC. The low volume capability, high separation efficiency, and sensitive detection schemes make CZE a powerful method for analytic biotechnology, the critical need for today's bioindustry.

The capillary of the apparatus may be a simple fused silica tube. Other capillaries, made of plastic, silica, or other nonconductive materials, can be equally used. Because the process employed using the apparatus reduces or substantially eliminates interior wall adsorption of molecules, no interior coating need be used, but of course, if the specific application contemplated requires such a coating, it can be applied.

The capillary tube bears a conductive member exterior to the interior of the capillary tube. By this, it is intended that the conductive members can be located within the thickness of the tube, on the exterior surface, or distanced from the exterior surface of the tube. Thus, the tube may bear a metal or conductive coating applied to the exterior surface of the tube. Typically, vacuum vapor deposition of, e.g., a metal or metal oxide may be used for this. Alternatively, if the cost is justified, the tube may be fabricated with the conductive member within the thickness of the tube, provided it is not present on the interior surface of the tube. Such conductive members might include a layer of metallic or carbon/graphitic fibers molded within the thickness of the tube, with an extension to the exterior of the tube for connection to an electrical generator of some type.

In a simple, alternative embodiment, the capillary tube may be encased in an outer vessel, the annulus between being filled with a conductive liquid, such as a buffer of some type. Accordingly, the nature and placement of the conductive member exterior to the interior surface of the capillary tube is not critical, and all equivalents of the embodiments described herein are contemplated for use in the invention. A preferred embodiment involves the preparation of, a conductive member actually coated about, or adhered to, the exterior surface of the capillary tube.

Figure 1:
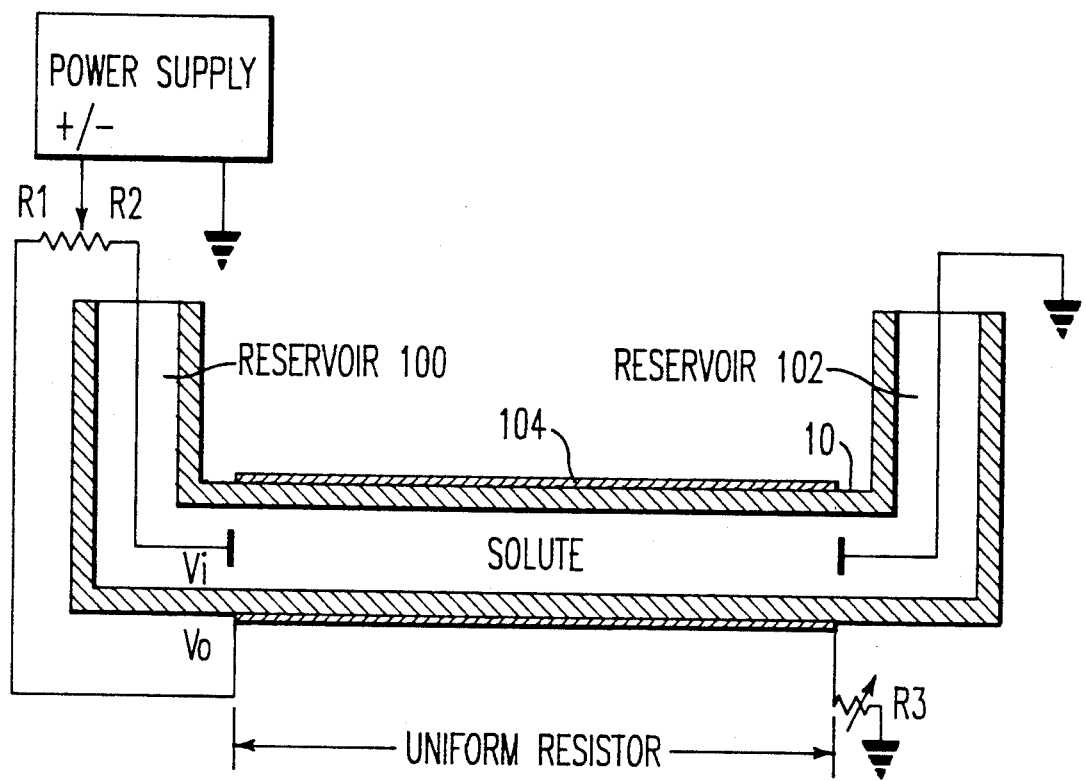
FIG. 1 is a diagrammatic illustration of one embodiment of the apparatus, bearing a conductive member exterior to the capillary tube for the application of an external electric field.
Figure 2A:
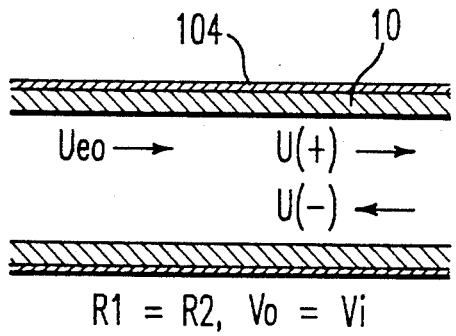
FIG. 2 is a diagrammatic illustration of the apparatus of FIG. 1, illustrating alternative connections, voltages and resulting electroosmotic flow.
Figure 2B:
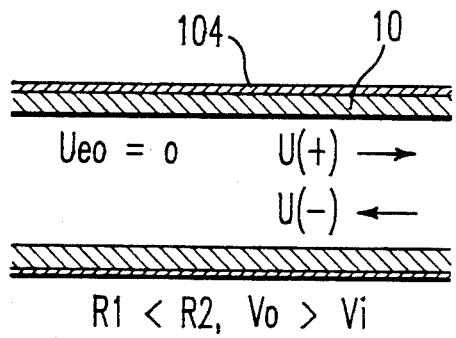
Figure 2C:
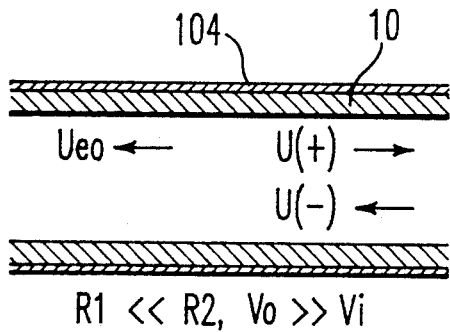
Figure 2D:
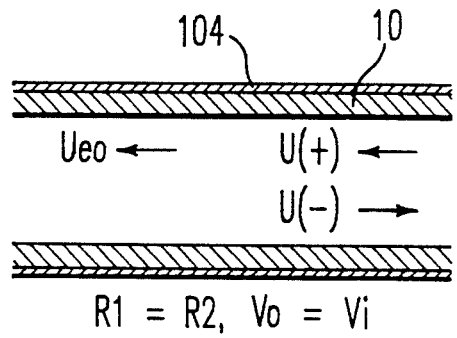
Figure 2E:
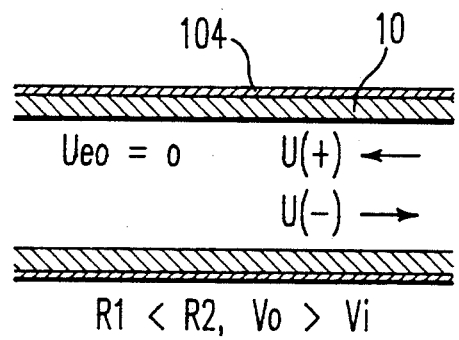
Figure 2F:
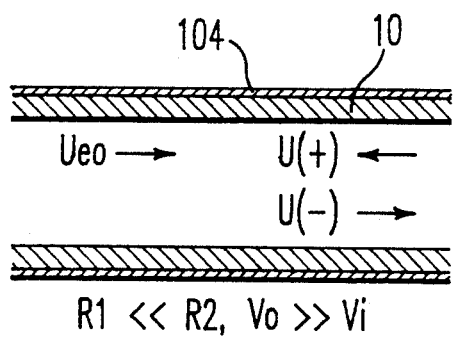

The use of the capillary electrophoresis apparatus of the claimed invention is not substantially different from conventional capillary electrophoresis processes, save for the application of external electric field across the tube. Thus, referring to FIG. 1, the tube 10, of conventional length and diameter (i.d. less than 1 millimeter, length typically 10-1000 millimeters) is filled with the buffer of choice. The ends of the tube are connected to reservoirs 100, 102 containing the same buffer. Into reservoir 100, the solution or suspension bearing the mixtures to be separated is added, by injection, syphon, etc. Reservoir 100 is hooked up to voltage, and the remainder 102 is connected, by electrode or other electrical connection, to ground. At the reservoir where the sample is not introduced, there is a detector of some type (not illustrated), to determine the time and amount of solute migration. The determination as to whether to hook up the sample reservoir, or the reservoir provided with the detector, to the positive or negative voltage is made principally on the basis of the charge of the particle of interest, the direction of the applied field determining the direction of electroosmotic flow. This is conventional capillary electrophoresis.

Pursuant to the invention of this application, in addition to the connection of the reservoirs to a voltage source, a conductive member 104 exterior to the interior surface of the tube is along the tube, and hooked up to a source of electrical voltage, such that the members, when electrified, create an external electric field across the exterior of the capillary. When there is a difference between this external potential, $V_o$ and the internal electric potential $V_i$ inside the capillary, a potential gradient is exerted across the capillary tube. As illustrated, R1 is hooked up to a voltage source, while R3 is connected to ground. The ratio of R2 to R1 determines the electric potential gradient or difference between the external electric potential, Vo and the internal electric potential, Vi. The resistance value of R3 ensures that the potential gradient across the capillary is uniform and constant along the length of the capillary coated with conductive member 104.

Actual application of an external electric field across the interior of the tube has been achieved in a plurality of embodiments, including an embodiment where the capillary tube passes through, but is not in fluid communication with, an annular reservoir of buffer identical to the buffer provided in the reservoirs at the open ends of the tube. Application of voltage to such an encircling reservoir of a value identical to that of the linear field results in a sharp reduction in the electroosmotic flow rate of about $\frac{1}{3}$. Where the applied linear potential Vi is 5.5 kV, application of an external potential Vo through the conductive member through which the capillary tube passes but as to which is not in fluid communication reduces electroosmotic flow of about 8 kV reduces electroosmotic flow by a factor of three. Applying increased voltage to the conductive members about the exterior of the capillary tube can virtually halt the electroosmotic flow, and upon the application of even higher voltages, reverse the direction of electroosmotic flow. Of course, application of potentials of opposite sign can result in enhanced electroosmotic flow. Thus, the flow conditions of any apparatus can be specifically tailored, using the claimed invention, to achieve enhanced resolution.

Figure 5A:
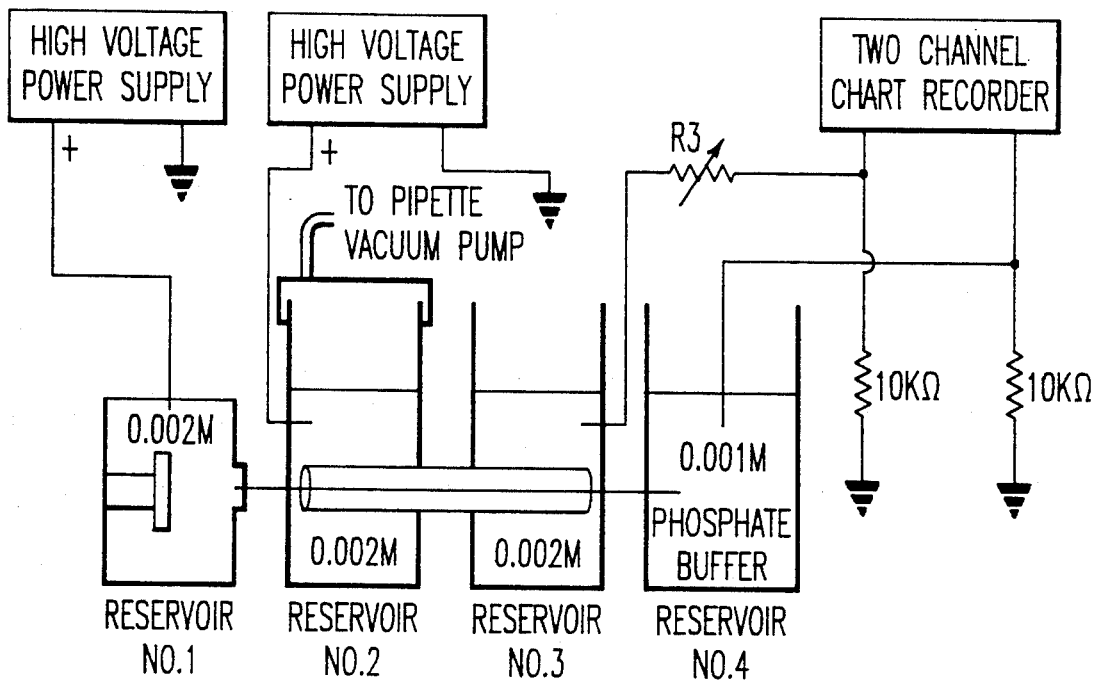
FIG. 5 is a diagrammatic illustration of an alternative embodiment of the invention, shown connected in two different fashions (a) and (b).
Figure 5B:
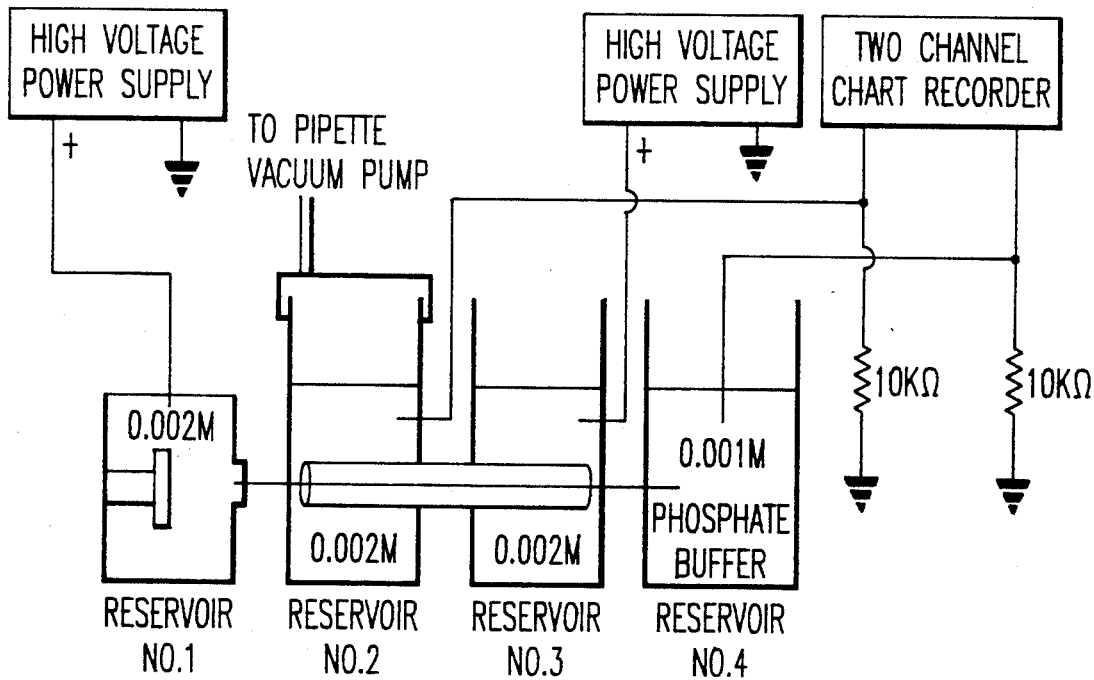

Actual application of an external electric field has been achieved in a set up shown in FIG. 5. A 20 cm long capillary (Polymicro Technologies, Inc. Phoenix, Ariz.) with 75 microns o.d.) was placed inside a larger capillary (530 microns i.d., 630 microns o.d.) which is 17 cm long. The smaller (inner) capillary was attached between reservoir 1 and reservoir 4 while the larger (outer) capillary was attached between reservoir 2 and reservoir 3. The polyamide coating on the exterior surfaces of both inner and outer capillaries were removed by using concentrated sulfuric acid solution. A syringe was used as reservoir 1 and as a pumping device for flushing out air bubbles from the inner capillary. Platinum wire electrodes were affixed to all four reservoirs.

Reservoir 2, reservoir 3, and the annulus between the inner and outer capillaries were filled with 0.002 M potassium phosphate buffer at a pH of about 6. One high voltage power supply connecting to reservoir 2 or reservoir 3 so that an external field can be applied in the annual space between two capillaries. A pipet vacuum pump was used to accelerate the fluid flow in the annulus between the inner and outer capillaries. This is to enhance the heat transfer in the annulus for removing the additional heat generated by the application of an external electric field. Another high voltage power supply connecting reservoir 1 with reservoir 4 applied an electric field (inner) inside the inner capillary. With adjustable resistor R3, we were able to establish various potential gradients between the inner and outer electric fields along the 17 cm long annulus between reservoir 2 and reservoir 3. The resulting changes in the direction and speed of electroosmotic flow in the inner capillary were monitored using the current-monitoring method developed by Zare et al.

The effect of external electric field on the direction and magnitude of electroosmotic flow is summarized in Table 1. The flow rate of the electroosmosis from reservoir 1 to reservoir 4 increases from 3.73+0.22 cm/min with application of −5 kV potential gradient between the outer and inner fields along the 17 cm long annulus. Applying positive potential gradients from 0 to 5 kV between the outer and inner fields starts to reduce the flow rate of the electroosmosis, and virtually halts the electroosmotic flow. The direction of electroosmotic flow can be even reversed (from reservoir 4 to reservoir 1) at even higher positive potential gradient, 6 kV.

The absolute value of zeta potential at the aqueous inner capillary interface is calculated. The cathode end of the inner electric field is set in reservoir 4. Thus, the zeta potential would be negative if the direction of electroosmosis is from reservoir 1 to reservoir 4. The zeta potential changes from −29 mV without external field to −35 mV with −5 kV potential gradient. The absolute value of the zeta potential decreases from −29 mV without external field to about 0 mV with +5 kV potential gradient. The polarity of the zeta potential can be even reversed at +6 kV potential gradient.

TABLE 1

| THE EFFECT OF EXTERNAL ELECTRIC FIELD ON THE ELECTROOSMOSIS | | | | | | | |
|---|---|---|---|---|---|---|---|
| INNER POTENTIALS[a] | | | OUTER POTENTIALS[b] | | POTENTIAL GRADIENT[c] | ELECTROOSMOTIC | ZETA[e] |
| Vi1 | Vi2 | Vi3 | Vo2 | Vo3 | V | FLOW RATE[d] | POTENTIAL |
| (Kv) | | | (Kv) | | (Kv) | (CM/MIN) | (mV) |
| 5.5 | 5 | 0.4 | 0 | −4.6 | −5 | +4.48 | −35 |
| 5.5 | 5 | 0.4 | 0 | 0 | No external field | +3.73 | −29 |
| 5.5 | 5 | 0.4 | 5 | 0.4 | 0 | +2.29 | −18 |
| 5.5 | 5 | 0.4 | 8 | 3.4 | +3 | +1.68 | −13 |
| 5.5 | 5 | 0.4 | 10 | 5.4 | +5 | ∼0 | ∼0 |
| 5.5 | 5 | 0.4 | 11 | 6.4 | +6 | −0.87 | +7 |

[a]Vi1, the inner potential at reservoir 1; Vi2, the inner potential at the beginning of the annulus (in reservoir 2) between the inner and outer capillaries; Vi3, the inner potential at the end of the annulus (reservoir 3). Vi2 and Vi3 are estimated by assuming a linear potential gradient inside the inner capillary.
[b]Vo2, the outer potential at the beginning of the annulus; Vo3, the outer potential at the end of the annulus.
[c]Vo2 − Vi2 or Vo3 − Vi3. The gradient is uniform through the annulus.
[d]Electroosmosis in the inner capillary with the cathode end in reservoir 4, + from reservoir 1 to reservoir 4, − from reservoir 4 to 1.
[e]See FIG. 5b for test set up. R3 = 0.
[f]See FIG. 5a for test set up. The value of R3 is such that a uniform potential gradient is obtained between the inner and outer electric fields along the 17 cm long annulus.

Figure 3:
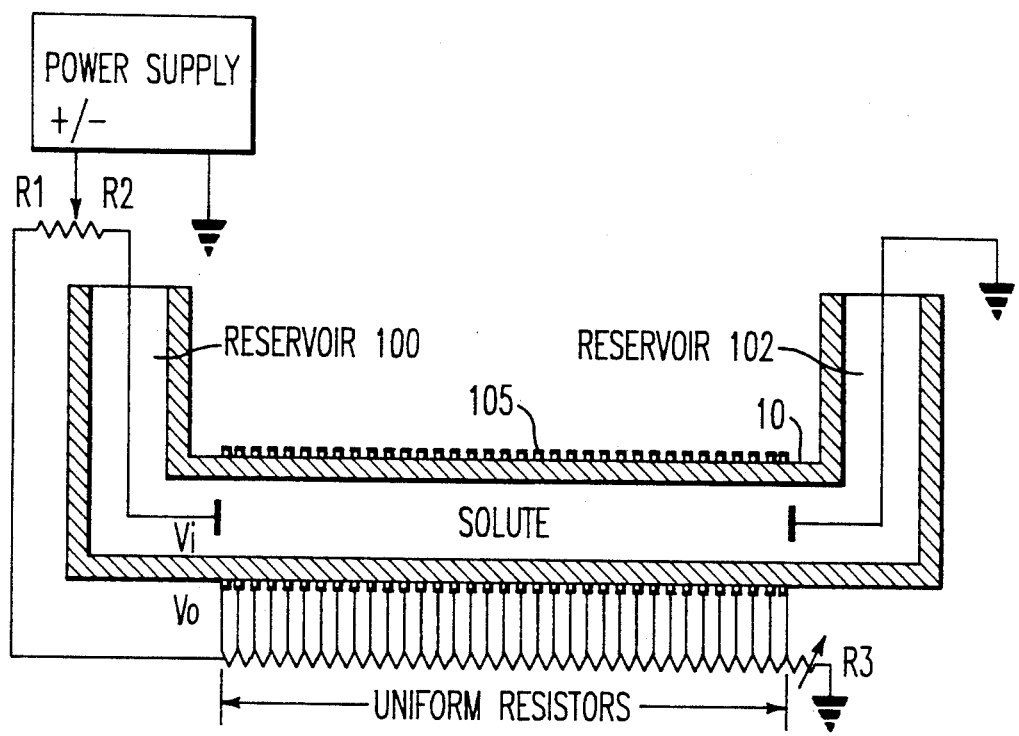
FIG. 3 is a diagrammatic illustration of an alternative embodiment bearing a plurality of conductive members all uniformly attached to voltage.
Figure 4:
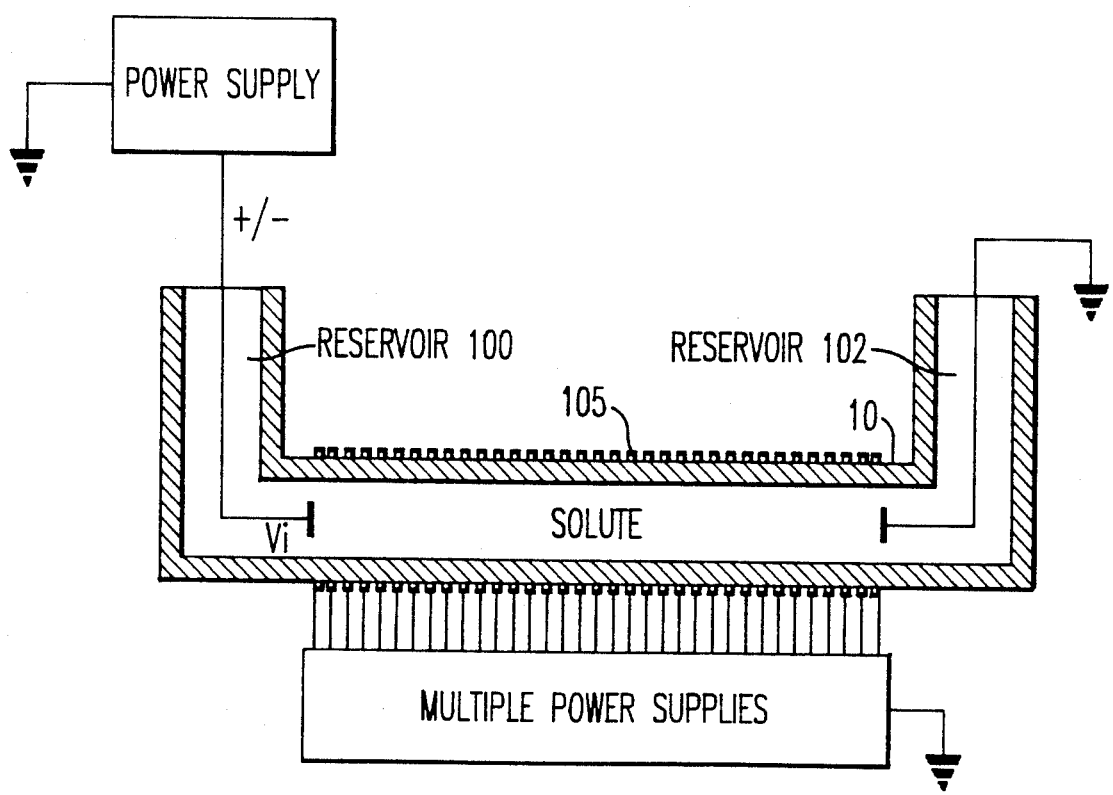
FIG. 4 is an illustration of the apparatus of FIG. 3 where the conductive members are separately connected to independent voltage sources.

As illustrated in FIG. 3, the conductive member that constitutes the means for applying an electric field across the capillary need not be monolithic. In FIG. 3, the means comprises a plurality of conductive rings deposited about the capillary, and circumferential manner, again, through vacuum coating processes and the like. In general, and particularly for CZE, it is desirable to maintain a constant potential gradient between the external and internal electric fields. Thus, in FIG. 3, all conductive rings 105 (referred to as uniform resistors) are connected to a single power source, giving rise to a uniform gradient across the tube 10.

For other applications, it may be desirable to alter the gradient along the tube. Such a process can be practiced with the embodiment illustrated in FIG. 3, wherein each ring 105, or a group of rings 105, is connected to a separate power supply, independently variable. By so varying the field applied across the tube, zones of different electroosmotic flow and electrophoretic mobility can be created, to enhance resolution.

When rings or other discrete conductive members are used, longitudinal spacing between the rings is preferably less than the wall thickness of the tube. The impedance of the source of the potential applied to the exterior of the capillary must be small with respect to the impedance of the source of the potential of the electrolyte solution inside the capillary, along the entire length of the capillary.

This invention has been disclosed in terms of both general and specific embodiment description. Those of ordinary skill in the art will arrive at further alternative embodiments, without the exercise of inventive skill. In particular, descriptions of materials, compositions, electrical voltage values, dimensions and the like, are not limiting, unless so indicated. The invention remains unlimited save for the parameters recited in the claims appended below.

What is claimed is:

1. A method of separating elements of a mixture of substances in a solution or suspension by conducting capillary electrophoresis of said solution or suspension, said electrophoresis inducing an electroosmotic flow in said solution or suspension, said method comprising:
   1) applying an internal electric field internally along the length of a capillary tube having an interior filled with said solution or suspension bound by a capillary wall,
   2) applying an external electric field across the interior of said capillary tube through a conductive member exterior to the interior of said capillary tube,
   3) wherein the electric potential difference between the internal and external fields produces an electric field perpendicularly across the capillary wall, along the length of said tube, thereby altering the electroosmotic flow rate, and
   4) permitting said solution to undergo electrophoresis under the influence of said electric fields, whereby separation of said elements is optimized.

2. The process of claim 1, wherein said element comprises biomolecules.

3. The process of claim 1, wherein said element comprises protein molecules.

4. The process of claim 1, wherein said process further comprises forming micelles in said suspension which micelles are resolved by micellar capillary electrophoresis.

5. The process of claim 1, wherein said electric potential difference is non-uniform along the length of said tube.

6. The method of claim 1, wherein the absolute value in the electric potential difference is up to 6 Kv.

7. The process of claim 3, wherein said capillary tube comprises silica, and said interior surface is free of any coating on said silica.

8. A method for improving resolution of components of a liquid composition comprising a solution or suspension through capillary electrophoresis, comprising:
   1) filling a capillary tube with said liquid composition,
   2) applying an internal electric field along the length of said capillary tube to cause components in said liquid composition to undergo electrophoretic migration in the direction of said internal field, thereby inducing electroosmotic flow in said tube, and
   3) altering said electrophoretic migration by applying an electric field across the interior of said capillary tube from a source exterior to said tube, thereby causing the electroosmotic flow induced to change, improving resolution of the components of said suspension.

9. The method of claim 8, wherein said electroosmotic flow rate is increased.

10. The method of claim 8, wherein said electroosmotic flow rate is decreased.

11. The method of claim 8, wherein the strength of said electric field applied across the interior of said capillary is altered during said resolution process.

12. The method of claim 8, wherein said field applied across the capillary tube in step c is of such dimension as to halt electroosmotic flow in said tube.

13. The method of claim 8, wherein said field applied across the capillary tube in step c is of dimension sufficient to reverse the direction of said induced electroosmotic flow.

* * * * *